(12) United States Patent
Murayama

(10) Patent No.: US 10,478,049 B2
(45) Date of Patent: Nov. 19, 2019

(54) ENDOSCOPE

(71) Applicant: OLYMPUS CORPORATION, Tokyo (JP)

(72) Inventor: Masahiko Murayama, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/032,136

(22) Filed: Jul. 11, 2018

(65) Prior Publication Data

US 2018/0325361 A1 Nov. 15, 2018

Related U.S. Application Data

(63) Continuation of application No. PCT/JP2016/079987, filed on Oct. 7, 2016.

(30) Foreign Application Priority Data

Jan. 13, 2016 (JP) ................................. 2016-004475

(51) Int. Cl.
*G02B 6/06* (2006.01)
*A61B 1/00* (2006.01)
(Continued)

(52) U.S. Cl.
CPC ........ *A61B 1/00167* (2013.01); *A61B 1/0011* (2013.01); *A61B 1/0052* (2013.01);
(Continued)

(58) Field of Classification Search
CPC .................................... G02B 6/06; A61B 1/00
(Continued)

(56) References Cited

U.S. PATENT DOCUMENTS 4,784,144 A * 11/1988 Ono .................... A61B 1/00165
385/117
4,805,598 A * 2/1989 Ueda .................. A61B 1/00091
359/665

(Continued)

FOREIGN PATENT DOCUMENTS

EP 2740400 A1 6/2014
JP H06-500183 A 1/1994

(Continued)

OTHER PUBLICATIONS

International Search Report dated Dec. 13, 2016 issued in PCT/JP2016/079987.

*Primary Examiner* — Kaveh C Kianni
(74) *Attorney, Agent, or Firm* — Scully, Scott, Murphy & Presser, P.C.

(57) ABSTRACT

An endoscope includes a distal end rigid portion including a through hole, an elongated image pickup section, a distal end of which is inserted and fixed in the through hole, a light guide fiber bundle, distal end molded portions of which are inserted and fixed in the through hole, the light guide fiber bundle being formed as one bundle from a proximal end portion to a predetermined branched portion on a distal end side, and formed by being branched into a plurality of bundles on a distal end side with respect to the predetermined branched portion; a plurality of first cover tubes made of e-PTFE, and respectively covering the plurality of bundles from the distal end molded portions to the predetermined branched portion; and one second cover tube of a material other than the e-PTFE, covering the one bundle from the predetermined branched portion to the proximal end portion.

6 Claims, 8 Drawing Sheets

(51) Int. Cl.
   *G02B 23/26* (2006.01)
   *A61B 1/005* (2006.01)
   *A61B 1/07* (2006.01)
   *G02B 6/36* (2006.01)
   *G02B 23/24* (2006.01)

(52) U.S. Cl.
   CPC ........ *A61B 1/0055* (2013.01); *A61B 1/00096* (2013.01); *A61B 1/00188* (2013.01); *A61B 1/07* (2013.01); *G02B 23/26* (2013.01); *G02B 6/06* (2013.01); *G02B 6/3624* (2013.01); *G02B 23/2469* (2013.01)

(58) Field of Classification Search
   USPC .......................................................... 385/117
   See application file for complete search history.

(56) References Cited

U.S. PATENT DOCUMENTS

| | | | |
|---|---|---|---|
| 5,002,359 A | | 3/1991 | Sayegh |
| 5,159,920 A * | | 11/1992 | Condon ................. A61B 1/042 600/121 |
| 5,182,785 A | | 1/1993 | Sayegh et al. |
| 5,634,790 A * | | 6/1997 | Pathmanabhan .. A61B 1/00087 433/29 |
| 5,695,447 A * | | 12/1997 | Yabe ................. A61B 1/00142 600/121 |
| 6,687,010 B1 * | | 2/2004 | Horii ................... G01B 9/0201 356/479 |
| 2002/0168317 A1 * | | 11/2002 | Daighighian .......... A61K 49/18 424/1.11 |
| 2004/0220451 A1 * | | 11/2004 | Gravenstein ......... A61B 1/0017 600/139 |
| 2005/0182297 A1 * | | 8/2005 | Gravenstein ......... A61B 1/0017 600/139 |
| 2005/0192480 A1 * | | 9/2005 | Toriya ................ A61B 1/00167 600/182 |
| 2006/0025691 A1 * | | 2/2006 | Tanaka ..................... A61B 8/12 600/459 |
| 2006/0132790 A1 * | | 6/2006 | Gutin .................. A61B 5/0066 356/479 |
| 2007/0287920 A1 * | | 12/2007 | Sawada ..................... A61B 8/12 600/463 |
| 2008/0058629 A1 * | | 3/2008 | Seibel .................. A61B 1/0008 600/368 |
| 2008/0262359 A1 * | | 10/2008 | Tearney ............. A61B 1/00096 600/476 |
| 2009/0177094 A1 * | | 7/2009 | Brown ................. A61B 5/0066 600/476 |
| 2009/0187098 A1 * | | 7/2009 | Makower ............... A61B 5/411 600/424 |
| 2012/0191021 A1 * | | 7/2012 | Sobol ................... A61B 18/201 601/15 |
| 2013/0102846 A1 * | | 4/2013 | Sjostrom .................. A61B 1/07 600/110 |
| 2014/0036271 A1 * | | 2/2014 | Backman ............ G01N 21/474 356/446 |
| 2014/0163321 A1 | | 6/2014 | Seto et al. |
| 2017/0010456 A1 * | | 1/2017 | Gopinath ............. G02B 23/243 |
| 2018/0014773 A1 * | | 1/2018 | Barton ................. A61B 5/6847 |

FOREIGN PATENT DOCUMENTS

| | | |
|---|---|---|
| JP | H07-503079 A | 3/1995 |
| JP | H07-308283 A | 11/1995 |
| JP | H08-187219 A | 7/1996 |
| JP | H11-056763 A | 3/1999 |
| JP | 5112575 B2 | 1/2013 |
| JP | 2015-136441 A | 7/2015 |
| WO | WO 91/19211 A2 | 12/1991 |
| WO | WO 93/07521 A1 | 4/1993 |
| WO | WO 2013/190910 A1 | 12/2013 |

* cited by examiner ured to allow observation of an organ or the like by
ENDOSCOPE

CROSS REFERENCE TO RELATED APPLICATION

This application is a continuation application of PCT/JP2016/079987 filed on Oct. 7, 2016 and claims benefit of Japanese Application No. 2016-004475 filed in Japan on Jan. 13, 2016, the entire contents of which are incorporated herein by this reference.

BACKGROUND OF THE INVENTION

1. Field of the Invention

The present invention relates to a medical or industrial endoscope.

2. Description of the Related Art

Conventionally, endoscopes configured by including an elongated tubular-shaped insertion section are widely used in medical and industrial fields, for example. Among such endoscopes, a medical endoscope used in the medical field is configured to allow observation of an organ or the like by having the insertion section inserted into a body cavity of a subject, such as a living body, and to allow various treatments to be performed on the organ or the like as necessary by use of a treatment instrument inserted in a treatment instrument insertion channel of the endoscope. Furthermore, an industrial endoscope used in the industrial field is configured to allow insertion of the insertion section into an object such as a device or mechanical equipment, such as a jet engine or factory pipes, and to allow observation of a state, such as a state of a flaw or corrosion, inside the object, inspection or the like.

Such a conventional endoscope includes means for radiating illumination light from a distal end portion of the insertion section inserted into a subject, toward an observation target object. Such illumination means is configured by including a light guide fiber bundle which is a light guide member for guiding illumination light emitted by an illumination device through the insertion section and to the distal end portion of the insertion section, and an illumination optical system for emitting the illumination light guided by the light guide fiber bundle from the distal end portion of the insertion section and toward the observation target object, for example. In such a case, the light guide fiber bundle adopts a structure according to which an outer surface of the light guide fiber bundle is covered by a tubular member, for example.

With an endoscope having such a configuration, various alterations are made to efficiently arrange the light guide fiber bundle in an inner space of the distal end portion, and to prevent an outer diameter of the distal end portion of the endoscope from being increased. Various techniques such as molding of the light guide fiber bundle, which is inserted into the insertion section, to have a cross-sectional shape other than a simple circular shape are proposed, for example, by Japanese Patent No. 5112575.

With an endoscope disclosed in Japanese Patent No. 5112575, for example, a cover tube is molded at the same time when molding a distal end part of the light guide fiber bundle such that the cover tube and the distal end part of the light guide fiber bundle are molded to have a substantially same shape.

SUMMARY OF THE INVENTION

An endoscope according to an aspect of the present invention includes a distal end rigid portion provided at a distal end of an insertion section, and including a through hole penetrating from inside to outside; an elongated image pickup section provided inside the insertion section, a distal end of the image pickup section being fixed in a state of being inserted in the through hole; a light guide fiber bundle provided inside the insertion section, and including distal end molded portions each having a distal end molded to have an outer shape that is specified in advance in relation to another component inside the insertion section, the distal end molded portions being inserted and fixed in the through hole, the light guide fiber bundle being formed as one bundle from a proximal end portion to a predetermined branched portion on a distal end side, and formed by being branched into a plurality of bundles on a distal end side with respect to the predetermined branched portion; a plurality of first cover tubes made of expanded polytetrafluoroethylene, and respectively covering the plurality of bundles from the distal end molded portions to the predetermined branched portion; and one second cover tube of a material other than the expanded polytetrafluoroethylene, covering the one bundle from the predetermined branched portion to the proximal end portion.

DETAILED DESCRIPTION OF THE PREFERRED EMBODIMENT

Figure 1:
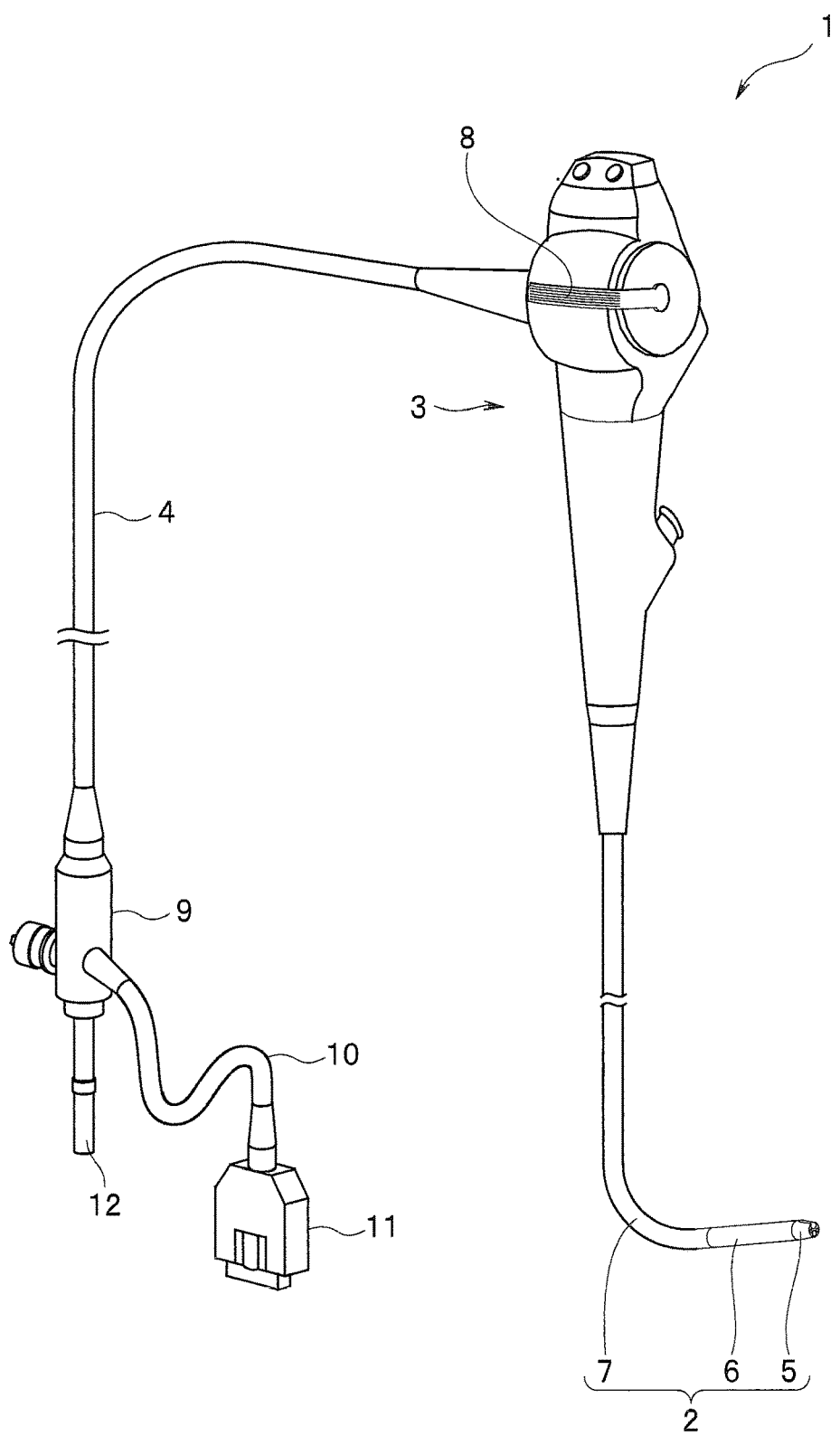
FIG. 1 is an external perspective view showing an endoscope according to an embodiment of the present invention.

Hereinafter, the present invention will be described with reference to an embodiment shown in the drawings. Each drawing used in the following description is schematic, and a dimensional relationship of respective members, scales and the like may be shown differently for each constituent component such that each constituent component is shown to be approximately large enough to be recognizable in the drawings. Accordingly, the present invention is not limited to the modes shown in the drawings with respect to the number of constituent components, the shapes of the constituent components, the proportion of the sizes of the constituent components, the relative positional relationship of respective constituent components, and the like shown in the respective drawings.

Figure 2:
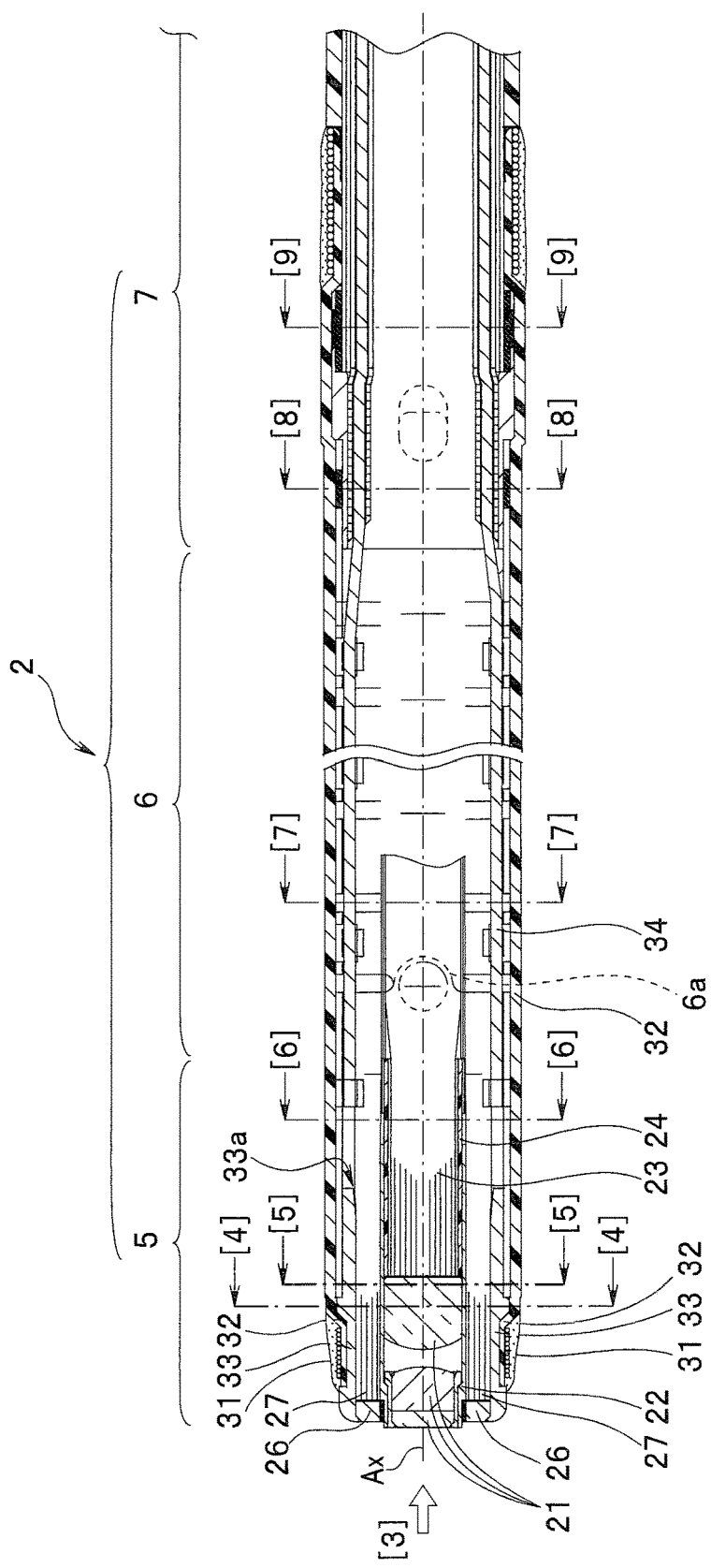
FIG. 2 is a vertical cross-sectional view showing a cross section along an insertion axis of an insertion section of the endoscope in FIG. 1.
Figure 3:
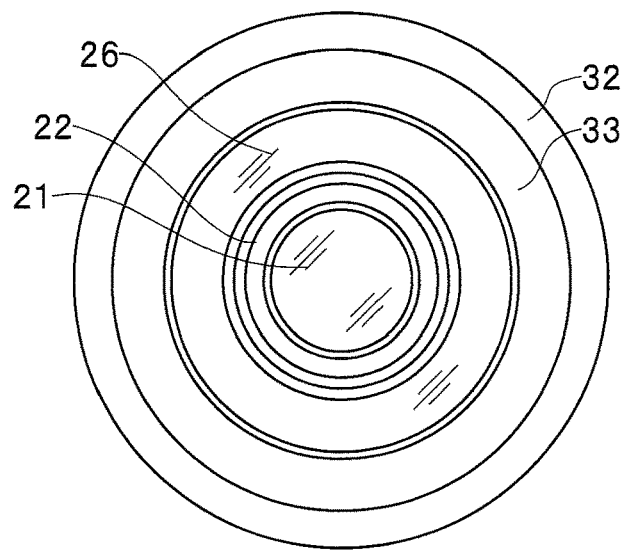
FIG. 3 is a plan view seen from a direction of an arrow [3] in FIG. 2.
Figure 4:
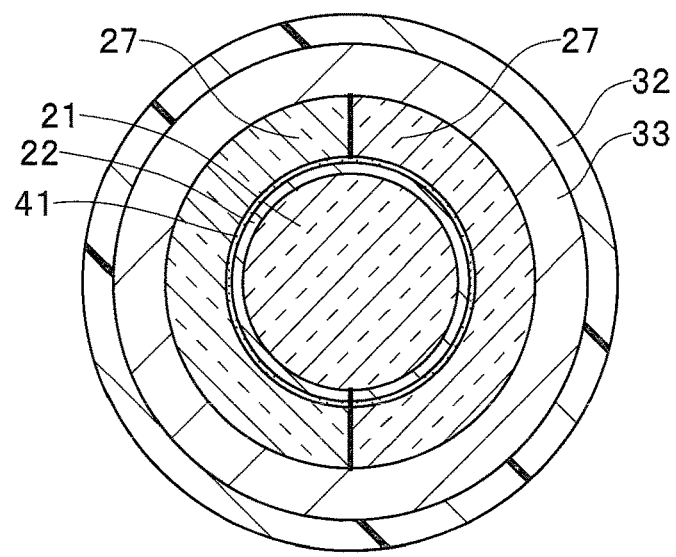
FIG. 4 is a cross-sectional view taken along a line [4]-[4] in FIG. 2.
Figure 5:
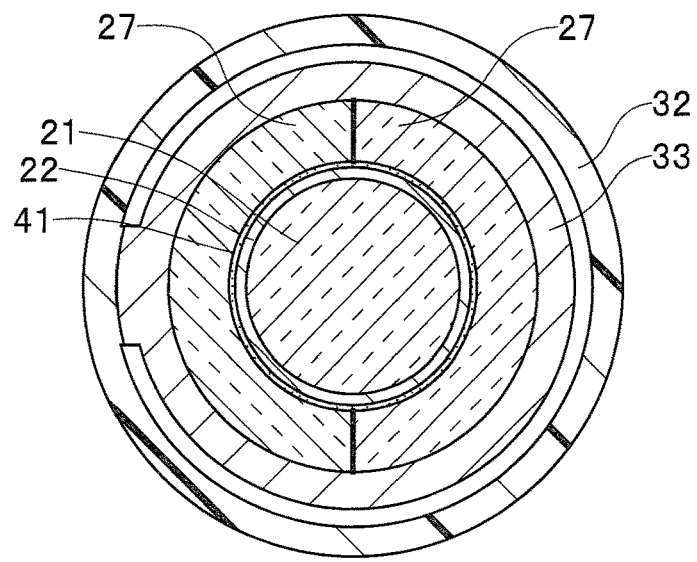
FIG. 5 is a cross-sectional view taken along a line [5]-[5] in FIG. 2.
Figure 6:
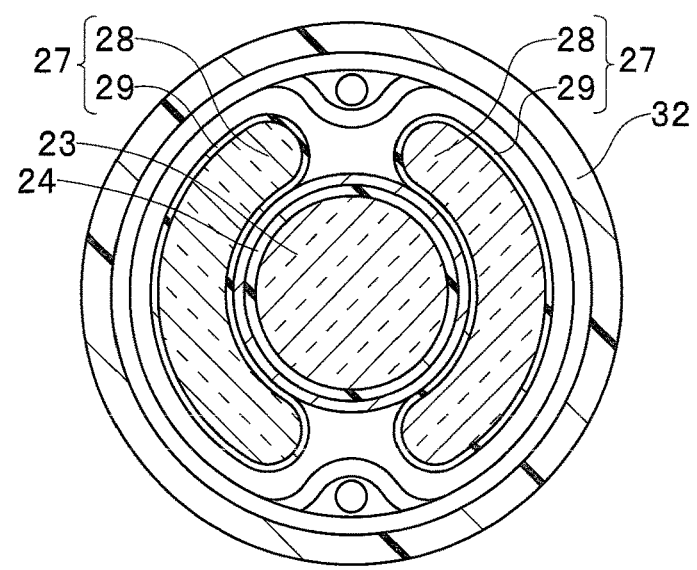
FIG. 6 is a cross-sectional view taken along a line [6]-[6] in FIG. 2.
Figure 7:
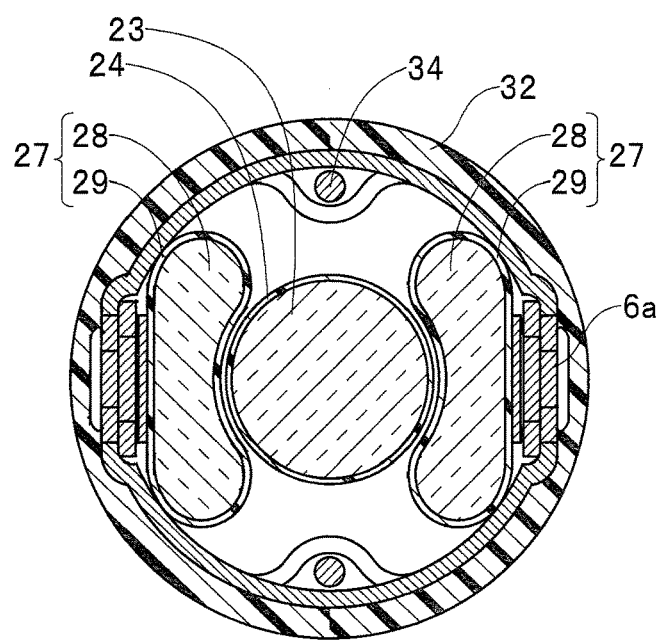
FIG. 7 is a cross-sectional view taken along a line [7]-[7] in FIG. 2.
Figure 8:
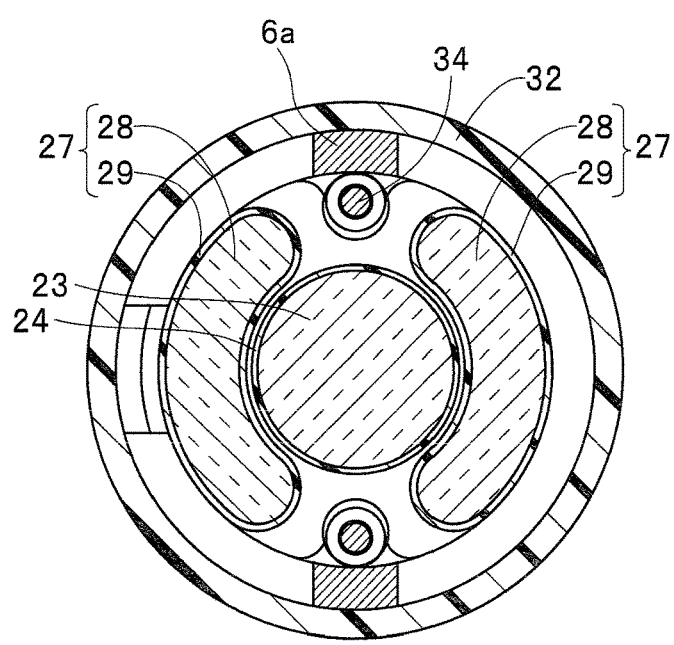
FIG. 8 is a cross-sectional view taken along a line [8]-[8] in FIG. 2.
Figure 9:
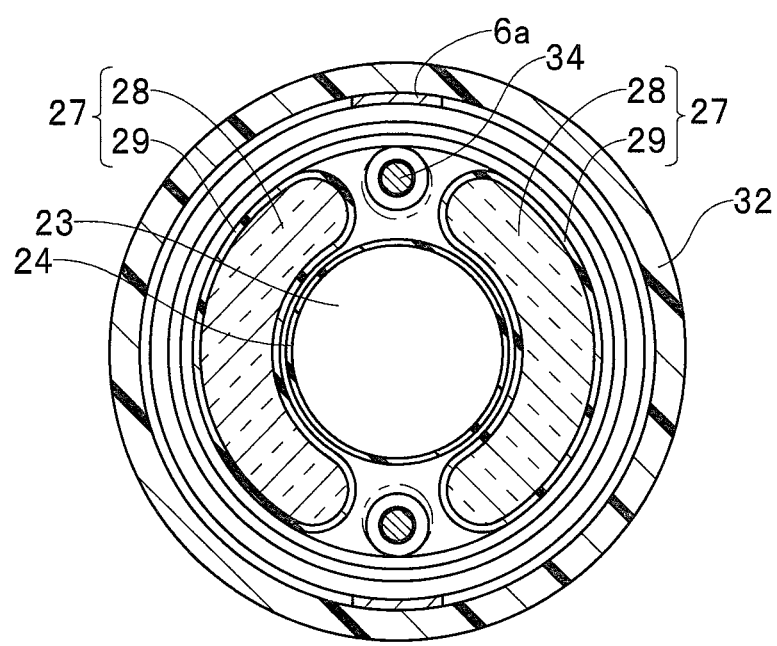
FIG. 9 is a cross-sectional view taken along a line [9]-[9] in FIG. 2.
Figure 10:
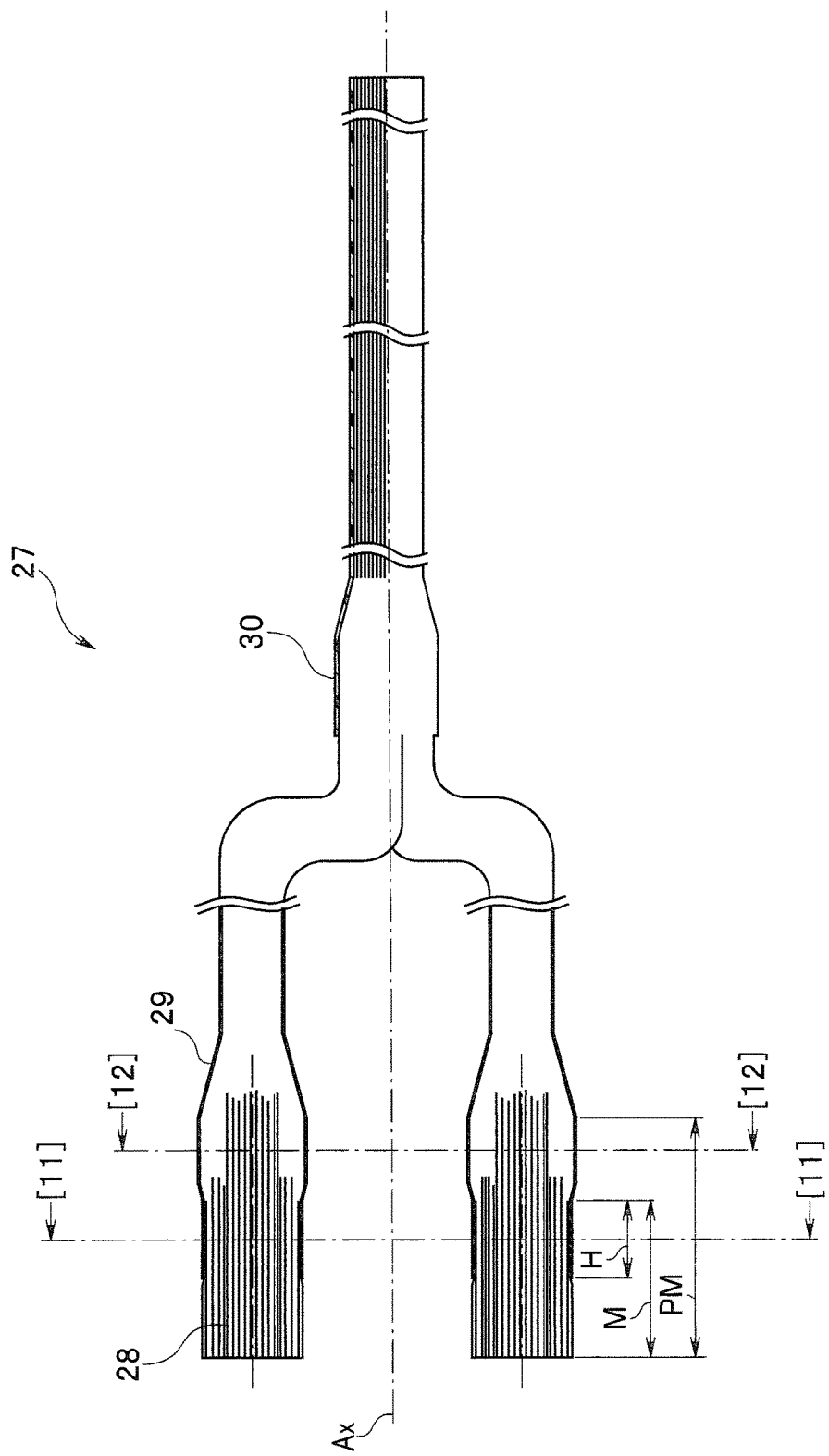
FIG. 10 is a half sectional view showing a cross section of only an upper half portion, along the insertion axis, of a light guide taken out of the endoscope in FIG. 1.
Figure 11:
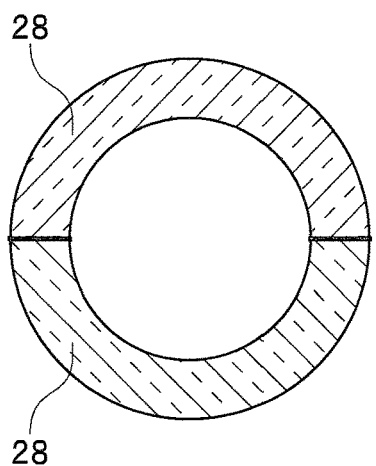
FIG. 11 is a cross-sectional view taken along a line [11]-[11] in FIG. 10.
Figure 12:
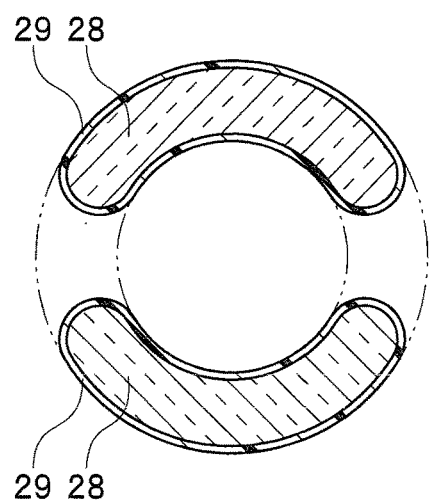
FIG. 12 is a cross-sectional view taken along a line [12]-[12] in FIG. 10.

FIG. 1 is an external perspective view showing an endoscope according to an embodiment of the present invention. FIG. 2 is a vertical cross-sectional view showing a cross section along an insertion axis of an insertion section of the endoscope in FIG. 1. FIG. 3 is a plan view seen from a direction of an arrow [3] in FIG. 2. FIGS. 4 to 9 are cross-sectional views of a plane perpendicular to the insertion axis of the insertion section of the endoscope in FIG. 1. Among the drawings, FIG. 4 is a cross-sectional view taken along a line [4]-[4] in FIG. 2. FIG. 5 is a cross-sectional view taken along a line [5]-[5] in FIG. 2. FIG. 6 is a cross-sectional view taken along a line [6]-[6] in FIG. 2. FIG. 7 is a cross-sectional view taken along a line [7]-[7] in FIG. 2. FIG. 8 is a cross-sectional view taken along a line [8]-[8] in FIG. 2. FIG. 9 is a cross-sectional view taken along a line [9]-[9] in FIG. 2. FIG. 10 is a half sectional view showing a cross section of only an upper half portion, along the insertion axis, of a light guide taken out of the endoscope in FIG. 1. FIG. 11 is a cross-sectional view of a distal end molded portion of the light guide in FIG. 10 (cross-sectional view taken along a line [11]-[11] in FIG. 10). FIG. 12 is a cross-sectional view of a fixed portion of the light guide in FIG. 10 (cross-sectional view taken along a line [12]-[12] in FIG. 10).

First, an overview of an overall configuration of an endoscope according to the present embodiment will be described below with reference mainly to FIG. 1. As shown in FIG. 1, an endoscope 1 of the present invention is configured of an insertion section 2 which is inserted into a subject, such as inside a body cavity, an operation section 3 which is provided in a linked manner on a proximal end side of the insertion section 2 and which serves also as a grasping section, and a universal cord 4 having flexibility and extending rearward from the operation section 3, for example.

The insertion section 2 is configured by including a distal end portion 5 provided with an objective optical system 21, an illumination optical system 26 and the like (described later; see FIG. 2, for example); a bending portion 6 which is formed to be bendable; a flexible tube portion 7 having flexibility; and the like; where the distal end portion 5, the bending portion 6, the flexible tube portion 7 and the like are provided in such an order from a distal end side.

The operation section 3 includes, on an inside, various components, such as electrical components including an electrical circuit board and an electrical cable (not shown), a bending mechanism (not shown) for bending the bending portion 6 of the insertion section 2, and various pipes, cables and the like (not shown) which are inserted through the universal cord 4 to the distal end portion 5 of the insertion section 2. Furthermore, various operation members, such as a bending lever 8 for bending the bending portion 6 in a remote manner, are disposed on an outer surface of the operation section 3. Note that a configuration of the operation section 3 is not directly relevant to the present invention, and thus, the operation section is assumed to have a same configuration as an operation section of a conventional endoscope, and illustration and detailed description of an internal configuration and components on an outer surface are omitted.

The universal cord 4 is a tubular member allowing insertion of a light guide (details described later; see FIGS. 2, 10, etc.) for transmitting illumination light from a light source illumination device (not shown), and signal cables (not shown), connected to a control unit (not shown), for transmitting various signals, for example. A light guide connector 9 which can be connected to the above-mentioned light source device (not shown), which is an external device, is connected to an end part of the universal cord 4. A light guide connection terminal 12 is provided at one end of the light guide connector 9.

Furthermore, a video cable 10 is branched to extend from a side surface of the light guide connector 9. A video connector 11 is connected to an end part of the video cable 10. The video connector 11 is connected to a camera control unit (CCU; not shown), which is a control device including a video processing function and the like and which is a signal processing device, for example. That is, the video connector 11 is a connection member for electrically connecting the camera control unit and the endoscope 1.

Next, an internal configuration of the insertion section 2 of the endoscope 1, or more particularly an internal configuration of the distal end portion 5, will be described below in detail with reference to FIGS. 2 to 12.

As described above and as shown in FIG. 2, the insertion section 2 of the endoscope 1 is configured by having the distal end portion 5, the bending portion 6, and the flexible tube portion 7 provided in a linked manner and in such an order from a distal end.

The distal end portion 5 is provided at the distal end of the insertion section 2, and is configured of a distal end rigid portion 33 which includes a through hole 33a penetrating from inside to outside and which is a hollow cylindrical member, and various constituent units provided inside the distal end rigid portion 33, namely, an observation system unit and an illumination system unit.

The observation system unit is a unit configured of an objective optical system 21 including a plurality of optical lenses, a lens holding frame 22 holding the plurality of optical lenses constituting the objective optical system 21 in such a way that respective optical axes of the respective optical lenses coincide with one another, an image guide fiber bundle 23 as an image pickup section, and an image pickup device such as a CCD (charge coupled device) image sensor or a CMOS (complementary metal oxide semiconductor) image sensor.

The objective optical system 21 is a lens group for collecting a light flux reflected by an observation target object inside a subject and for forming an optical image of the observation target object. A most distal optical lens of the objective optical system 21 is provided at a front surface of the distal end portion 5.

The image guide fiber bundle 23, which is an image pickup section, is a long member which is inserted and arranged inside the insertion section 2. A distal end of the image guide fiber bundle 23 is fixed, in a state of being inserted in the through hole 33a of the distal end rigid portion 33, at a rear of the objective optical system 21 and to an emitting surface from which light which is transmitted through the objective optical system 21 is emitted rearward.

An outer surface of the image guide fiber bundle 23 is covered by an image guide cover tube (hereinafter referred to as "IG cover tube") 24 which is flexible and which is formed into an elongated tubular shape. As the IG cover tube 24, a tubular member having flexibility and slipperiness, such as a tube member made of a material such as nylon, silicone, expanded polytetrafluoroethylene (e-PTFE; expanded PTFE), is used.

The image guide fiber bundle 23 is a transmitting member which is inserted through the insertion section 2 and the operation section 3 of the present endoscope 1, and which transmits an optical image from the objective optical system of the distal end portion 5 of the insertion section 2 to an eyepiece lens (not shown) provided at the operation section 3 (in a case where the endoscope 1 takes a fiberscope mode). Furthermore, in the case where the endoscope 1 takes a videoscope mode, a transmission cable is used instead of the image guide fiber bundle 23. The transmission cable is a transmitting member which transmits the following data of an image through the insertion section 2, the operation section 3 and the universal cord 4 and to the camera control unit (CCU; not shown). Here, an image is formed on a light receiving surface of an image pickup device (not shown) by the objective optical system of the distal end portion 5 of the insertion section 2 and the image is photoelectrically converted by the image pickup device.

The illumination system unit is a unit configured of the illumination optical system 26 and a light guide 27.

The illumination optical system 26 is an optical lens which is provided at the front surface of the distal end portion 5, and which is formed to have a substantially annular shape.

The light guide 27 is a long member which is inserted and arranged inside the insertion section 2. The light guide 27 is configured of the light guide fiber bundle 28, and light guide cover tubes (29, 30). Moreover, the light guide 27 is disposed on an outer peripheral side of the image pickup section, that is, the lens holding frame 22 and the image guide fiber bundle 23. Here, a periphery of a distal end part of the light guide 27 is bonded and fixed, by an adhesive 41, to an outer peripheral surface of the lens holding frame 22 (see FIGS. 4 and 5).

The light guide fiber bundle 28 is disposed while being compressed by the image guide fiber bundle 23 (image pickup section) across a first light guide cover tube (hereinafter referred to as "first LG cover tube") 29 in such a way that a minor axis is about 50% of a diameter of a case where the light guide fiber bundle 28 is formed to have a circular cross section. Note that the light guide fiber bundle 28 is assumed to be disposed while being compressed in such a way that the minor axis is about 50% of the diameter of a case where the light guide fiber is formed to have a circular cross section, but if a minor axis of a cross-sectional outer shape of the compressed light guide fiber bundle 28 is 20% to 90% of the diameter of the circular cross section, for example, the light guide fiber will not be broken, and the shape of the light guide fiber may be maintained.

The light guide fiber bundle 28 is configured by including a distal end molded portion (see a reference sign M in FIG. 10, and FIG. 11), a distal end of which is molded such that an outer shape has a non-circular cross section. Note that in the example described above, the outer shape of the distal end of the light guide fiber bundle 28 is assumed to be non-circular, but such an example is not restrictive, and a circular shape is also allowed, for example. The outer shape of the light guide fiber bundle 28 may take various shapes according to outer shapes of other components in the insertion section 2 where the light guide fiber bundle 28 is disposed, and thus, molding is performed to obtain a shape which is specified in advance for each model. As shown in FIG. 10, the light guide fiber bundle 28 is formed as one bundle in a length direction from a proximal end side, and is formed to have a shape which is branched into a plurality of parts from a predetermined position. In the present embodiment, an example is shown where the light guide fiber bundle 28 is branched into two parts from a predetermined position, but such an example is not restrictive, and the light guide fiber bundle 28 may be branched into three parts, four parts, or a greater number of parts, for example.

A distal end of the light guide fiber bundle 28 is fixed while being in contact with a rear end surface of the illumination optical system 26, in a state where the distal end molded portion M (see FIG. 10) is inserted inside the through hole 33a of the distal end rigid portion 33.

The light guide fiber bundle 28 is inserted through the insertion section 2, the operation section 3 and the universal cord 4 of the present endoscope 1, and extends through the distal end portion 5 of the insertion section 2 to the operation section 3, and up to the light guide connection terminal 12 at one end of the light guide connector 9 at the end part of the universal cord 4. That is, the light guide fiber bundle 28 is thereby made a transmitting member for transmitting, to the illumination optical system 26 of the distal end portion 5 of the insertion section 2, illumination light that is emitted by a light source illumination device (not shown) to which the light guide connection terminal 12 is connected.

Moreover, the outer surface of the light guide fiber bundle 28 is covered by the light guide cover tubes (29, 30; see FIG. 10) which are flexible and which are formed into elongated tubular shapes using predetermined materials (details are given later).

The first LG cover tube 29 covers the outer surface of the light guide fiber bundle 28 at a predetermined region including at least the distal end molded portion M, such as a region more on a distal end side than a branched portion. That is, the first LG cover tube 29 covers the light guide fiber bundle 28 from the distal end molded portion and at least inside the insertion section 2. As the first LG cover tube 29, a tube member which is formed using a material, a thickness of which can be particularly easily reduced and which has flexibility, such as expanded polytetrafluoroethylene (e-PTFE), is used.

Furthermore, the second light guide cover tube (hereinafter referred to as "second LG cover tube") 30 covers the outer surface at a part of a proximal end side of the light guide fiber bundle 28, that is, a predetermined region which is on the light guide connector 9 side and which is on the proximal end side with respect to the branched portion. As the second LG cover tube 30, a tube member which uses silicone as a material is used, for example.

Note that with the light guide 27 of the endoscope 1 of the present embodiment, the first LG cover tube 29 includes a fixed portion H (see FIG. 10) which is a region, at a region of the distal end molded portion M, adhered and fixed to the light guide fiber bundle 28. At the region of the fixed portion H, a diameter is formed to be substantially constant. The distal end molded portion M and the fixed portion H of the light guide 27 formed in the above manner are inserted and fixed inside the through hole 33a of the distal end rigid portion 33.

Moreover, at the time of molding a rigid molded portion PM (see FIG. 10) including the distal end molded portion M and the fixed portion H of the light guide 27, adhesion molding process is performed in a state where the light guide fiber bundle 28 is covered by the first LG cover tube 29.

An outer surface of the insertion section 2 is covered, across an entire length from the distal end rigid portion 33 to a proximal end portion, by an outer cover tube 32 having flexibility. Moreover, a distal end part of the outer cover tube 32 is bonded to an outer surface of the distal end rigid portion 33 in a watertight manner by so-called bobbin bonding.

The bending portion 6 is provided in a linked manner on a proximal end side of the distal end portion 5. The bending portion 6 is formed by providing a plurality of bending pieces 6a in a linked manner. A plurality of bending wires 34 inserted inside the insertion section 2 connect between the bending piece 6a at a most distal end of the bending portion 6 and a bending mechanism (not shown) inside the operation section 3. Note that a configuration of the insertion section 2 on a proximal end side with respect to the bending portion 6 is not directly relevant to the present invention, and thus, detailed illustration and description of the configuration are omitted, assuming that a same configuration as a configuration of a conventional endoscope is used.

As described above, according to the embodiment, a cover tube made of expanded polytetrafluoroethylene (e-PTFE), which is a material having desirable flexibility and a thickness of which can be easily reduced, is used as the first LG cover tube 29 of the light guide fiber bundle 28 at the light guide 27, across substantially entire length of a flexible portion of the insertion section 2, and thus, the light guide 27 may be efficiently arranged inside the insertion section 2. That is, even if the light guide 27 is compressed by another adjacent component inside the insertion section 2 at the time of being inserted inside the insertion section 2, the first LG cover tube 29 made of expanded polytetrafluoroethylene (e-PTFE) is superior in flexibility and may change shape in various ways, and thus, the light guide 27 may be efficiently arranged in a gap region in the insertion section 2 with no impairment of function.

Furthermore, at the time of molding the rigid molded portion PM including the distal end molded portion M of the light guide fiber bundle 28, adhesion molding of the light guide fiber bundle 28 and the first LG cover tube 29 can be simultaneously performed in a state where the light guide fiber bundle 28 is inserted and arranged in the first LG cover tube 29, and thus, manufacturing steps can be simplified compared with a conventional manufacturing method which uses a technique of molding a light guide fiber bundle and then covering the light guide fiber bundle by a cover tube and performing bonding.

Moreover, because the thickness of the first LG cover tube 29 made of expanded polytetrafluoroethylene (e-PTFE) can be easily reduced, a diameter of the distal end rigid portion 33 is not increased even if a portion covered by the first LG cover tube 29 is disposed inside the distal end rigid portion 33. Accordingly, a diameter of the distal end portion 5 of the insertion section 2 may be prevented from being increased. At the same time, an increase in a length of the distal end rigid portion 33 may be prevented, and the distal end rigid portion 33 may be made short.

Furthermore, a cross-sectional shape of the distal end molded portion M of the light guide fiber bundle 28 may be molded into a desired shape due to the flexibility of the first LG cover tube 29. Accordingly, the flexibility of the first LG cover tube 29 can contribute to realization of efficient arrangement of the light guide 27 inside the distal end portion 5 of the insertion section 2.

Note that the present invention is not limited to the embodiment described above, and it is needless to say that various modifications and applications are allowed without departing from the gist of the invention. Furthermore, the embodiment described above includes inventions of various stages, and various inventions may be extracted by appropriately combining a plurality of constituent elements disclosed herein. For example, even if some constituent elements are removed from all the constituent elements shown in the embodiment, when the problem to be solved by the invention can be solved and the advantageous effects of the invention can be achieved, a configuration from which the constituent elements are removed can be extracted as an invention. Moreover, constituent components of different embodiments may be combined as appropriate. The present invention is not limited by any specific embodiment, except as limited by the accompanying claims.

The present invention is applicable not only to an endoscope control device in the medical field, but also to an endoscope control device in the industrial field.

What is claimed is:

1. An endoscope comprising:
   a distal end rigid portion provided at a distal end of an insertion section, and including a through hole penetrating from inside to outside;
   an elongated image pickup section provided inside the insertion section, a distal end of the image pickup section being fixed in a state of being inserted in the through hole;
   a light guide fiber bundle provided inside the insertion section, and including distal end molded portions each having a distal end molded to have an outer shape that is specified in advance in relation to another component inside the insertion section, the distal end molded portions being inserted and fixed in the through hole, the light guide fiber bundle being formed as one bundle from a proximal end portion to a predetermined branched portion on a distal end side, and formed by being branched into a plurality of bundles on a distal end side with respect to the predetermined branched portion;
   a plurality of first cover tubes made of expanded polytetrafluoroethylene, and respectively covering the plurality of bundles from the distal end molded portions to the predetermined branched portion; and
   one second cover tube of a material other than the expanded polytetrafluoroethylene, covering the one bundle from the predetermined branched portion to the proximal end portion,
   wherein the plurality of bundles of the light guide fiber bundle formed on the distal end side with respect to the predetermined branched portion are disposed while being compressed by the image pickup section through the first cover tubes in such a way that minor axes are 90% or less of a diameter of a case where each bundle of the plurality of bundles is formed to have a circular cross section.

2. The endoscope according to claim 1, wherein the image pickup section is an image guide fiber bundle.

3. The endoscope according to claim 1, wherein an outer tube of the image pickup section is made of expanded polytetrafluoroethylene.

4. The endoscope according to claim 1, wherein the second cover tube is made of silicone.

5. The endoscope according to claim 1, wherein the light guide fiber bundle comprises, on a proximal end side of each of the distal end molded portions, a fixed portion to which each of the first cover tubes is adhered.

6. The endoscope according to claim 5, wherein:
   the light guide fiber bundle is disposed while a part of each of the plurality of bundles is compressed by the image pickup section through each of the first cover tubes in such a way that a minor axis is 90% or less of a diameter of a case where each of the plurality of bundles is formed to have a circular cross section, the part of each of the plurality of bundles being on the distal end side with respect to the branched portion and being on a proximal end side with respect to the fixed portion, and the distal end molded portions of the light guide fiber bundle are each molded such that the outer shape of the distal end is a non-circular shape.

\* \* \* \* \*